United States Patent
Siddiqui (10) Patent No.: US 9,956,381 B2
(45) Date of Patent: May 1, 2018

(54) CONCEPTS FOR CATHETER CONTROL AND STABILIZATION

(71) Applicant: FLORIDA ELECTROPHYSIOLOGY LLC, Orlando, FL (US)

(72) Inventor: Usman Siddiqui, Orlando, FL (US)

(73) Assignee: Florida Electrophysiology LLC, Orlando, FL (US)

( * ) Notice: Subject to any disclaimer, the term of this patent is extended or adjusted under 35 U.S.C. 154(b) by 282 days.

(21) Appl. No.: 14/862,764

(22) Filed: Sep. 23, 2015

(65) Prior Publication Data

US 2016/0089512 A1    Mar. 31, 2016

Related U.S. Application Data

(60) Provisional application No. 62/055,742, filed on Sep. 26, 2014.

(51) Int. Cl.
*A61M 25/01* (2006.01)
*A61M 25/00* (2006.01)

(52) U.S. Cl.
CPC .... *A61M 25/0113* (2013.01); *A61M 25/0097* (2013.01); *A61M 25/0136* (2013.01)

(58) Field of Classification Search
CPC .......... A61M 25/0113; A61M 25/0097; A61M 25/0136; A61M 25/0105; A61M 25/09041; A61M 25/013; A61M 2025/09125; A61M 2025/09116
See application file for complete search history.

(56) References Cited

U.S. PATENT DOCUMENTS

| | | | | |
|---|---|---|---|---|
| 5,161,534 A | * | 11/1992 | Berthiaume | A61M 25/01 226/127 |
| 7,736,337 B2 | * | 6/2010 | Diep | A61M 25/0097 604/164.01 |
| 8,808,248 B2 | * | 8/2014 | Schultz | A61B 17/3415 604/164.01 |
| 8,808,350 B2 | * | 8/2014 | Schreck | A61F 2/966 623/1.12 |
| 2009/0024085 A1 | * | 1/2009 | To | A61B 17/320758 604/95.01 |

(Continued)

OTHER PUBLICATIONS

STIC Search dated Dec. 8, 2017. Three (3) documents.*

*Primary Examiner* — Nathan R Price
*Assistant Examiner* — John Doubrava
(74) *Attorney, Agent, or Firm* — Alston & Bird LLP (57) ABSTRACT

A catheter guide device configured to facilitate precise placement of a downstream end of a catheter within a patient. The catheter guide device comprises a torque assembly configured to frictionally engage an exterior surface of a catheter and a hub configured to engage a catheter sheath and thereby prevent rotation of the catheter sheath relative to the hub. The torque assembly is rotatably secured to the hub such that rotating the torque assembly relative to the hub rotates the catheter relative to the catheter sheath and thereby moves the downstream end of the catheter within the patient. The hub additionally comprises a detent mechanism configured to engage a plurality of gear teeth on an exterior surface of the torque assembly to thereby impede unintended rotation of the torque assembly relative to the hub.

12 Claims, 3 Drawing Sheets

(56) References Cited

U.S. PATENT DOCUMENTS

2012/0078096 A1\* 3/2012 Krolik ............. A61B 17/22032
600/435
2012/0177436 A1\* 7/2012 LaBombard ...... A61M 25/0097
403/109.1

\* cited by examiner

CONCEPTS FOR CATHETER CONTROL AND STABILIZATION

CROSS-REFERENCE TO RELATED APPLICATIONS

This patent application claims priority to provisional U.S. Patent Ser. No. 62/055,742, filed Sep. 26, 2014, which is incorporated herein by reference in its entirety.

BACKGROUND

After inserting a catheter into a patient, surgeons and other medical professionals often must make precise changes to the direction of the catheter. Catheters are often inserted into a patient through a catheter sheath, and therefore such changes in the catheter direction often require the surgeon to rotate the catheter relative to the catheter sheath in order to facilitate proper placement. However, the smooth and small exterior diameter of the catheter, and the unpredictable level of force required to rotate the catheter relative to the catheter sheath when inside the patient may impede precise catheter placement.

Historically, medical professionals have manually rotated the catheter relative to the catheter sheath by hand. Because of the level of precision needed in placing a catheter, and the unpredictable amount of force necessary to rotate the catheter relative to the catheter sheath, it may be difficult to precisely align the catheter in the appropriate location within the patient. A surgeon may be required to make several precise changes in catheter positioning by moving a catheter to or from a particular location, and therefore the surgeon may be required to make many minor changes to the catheter placement relative to the catheter sheath during an adjustment process. Once the catheter reaches its proper positioning within the patient, the surgeon may then be required to ensure the catheter maintains its position for a period of time while other external forces (e.g., blood flows around the catheter, tissue retraction, and/or the like) may work to move the catheter away from its precise location.

Manually maintaining precise positioning by holding the catheter may be physically exhausting for a surgeon over a period of time, and therefore maintaining a precisely determined catheter placement may be difficult. Therefore, devices and methods for facilitating improved precision in catheter placement are needed in order to facilitate catheter stability.

BRIEF SUMMARY

Various embodiments are directed to a catheter guide device for facilitating precision positioning of a catheter inserted through a catheter sheath and into a patient. The catheter guide device comprising: a torque assembly configured to frictionally engage an exterior surface of the catheter to prevent rotation of the catheter relative to the torque assembly; and a hub rotatably secured to the torque assembly and configured to engage an upstream end of the catheter sheath and prevent rotation of the catheter sheath relative to the hub. In various embodiments, the hub is configured to engage a side port of a catheter sheath to prevent rotation of the catheter sheath relative to the hub, and may additionally comprise side port engagement features. The torque assembly defines a plurality of gear teeth on at least a portion of an exterior surface of the torque assembly; and the hub comprises a detent mechanism configured to operably engage the plurality of gear teeth of the torque assembly and thereby impede free rotation of the torque assembly relative to the hub such that rotating the torque assembly relative to the hub rotates the catheter within the catheter sheath so as to facilitate precision positioning of the catheter. In various embodiments, the gear teeth are spaced at regular intervals, such as at 1 mm intervals. In various embodiments, the torque assembly defines a lumen extending through the length of the torque assembly and configured to accept the catheter therein.

Moreover, in various embodiments the torque assembly comprises: a gear mechanism defining an exterior surface comprising the plurality of gear teeth; and a torque device detachably secured to the gear mechanism such that the torque device is prevented from rotating relative to the gear mechanism and configured to frictionally engage the exterior surface of the catheter. In various embodiments, the torque device is detachable from the gear mechanism while a catheter is positioned within the lumen extending through the torque assembly. The torque assembly may further comprise a locking ring rotatably secured to the gear mechanism and operable between: a locked position in which the torque device is prevented from detaching from the gear mechanism; and an unlocked position in which the torque device is permitted to detach from the gear mechanism.

Moreover, in various embodiments, the torque assembly further comprises an end cap detachably secured to the torque device at an upstream end of the torque device; and the upstream end of the torque device defines a plurality of jaw members configured to be compressed onto the exterior surface of the catheter to frictionally engage the catheter when the end cap is secured onto the torque device.

In various embodiments, the detent mechanism comprises a spring plunger biased to an extended position in which the spring plunger engages side surfaces of adjacent gear teeth to impede free rotation of the torque device relative to the hub; and wherein the spring plunger is configured to retract away from the extended position as a gear tooth passes the spring plunger.

In various embodiments, the torque assembly is configured to frictionally engage an exterior surface of an ultrasound catheter inserted through the catheter sheath to facilitate positioning of the ultrasound catheter within the patient. Moreover, in various embodiments, the torque assembly is configured to frictionally engage an exterior surface of an ablation catheter inserted through the catheter sheath to facilitate positioning of the ablation catheter within the patient.

Various embodiments area directed to a method of positioning a catheter within a patient. The method may comprise providing a catheter guide device comprising a torque assembly defining a plurality of gear teeth on at least a portion of an exterior surface of the torque assembly and defining a lumen extending through the length of the torque assembly; and a hub rotatably secured to the torque assembly, wherein the hub comprises a detent mechanism configured to operably engage the plurality of gear teeth of the torque assembly and thereby impede free rotation of the torque assembly relative to the hub; securing a catheter sheath to the hub of the catheter guide device to prevent rotation of the catheter sheath relative to the hub; inserting a catheter through the lumen of the torque assembly, through the catheter sheath, and into the patient; frictionally securing the torque assembly to an exterior surface of the catheter to prevent rotation of the catheter relative to the torque assembly; and rotating the torque assembly relative to the hub to rotate the catheter within the catheter sheath and the patient.

In various embodiments, the torque assembly comprises (i) a gear mechanism defining an exterior surface comprising the plurality of gear teeth, and (ii) a torque device detachably secured to the gear mechanism such that the torque device is prevented from rotating relative to the gear mechanism and configured to frictionally engage the exterior surface of the catheter, and the method further comprises disassembling the torque assembly while the catheter is inserted into the patient to retract the catheter within the patient. Moreover, in various embodiments, securing the catheter sheath to the hub of the catheter comprises: inserting a side port into the hub such that the side port is positioned within a side notch of the hub.

In various embodiments, an upstream end of the torque assembly defines a plurality of jaw members, and frictionally engaging the exterior surface of the catheter comprises securing an end cap onto the upstream end of the torque assembly, wherein the end cap compresses the plurality of jaw members onto the exterior surface of the catheter to frictionally engage the catheter when the end cap is secured onto the upstream end of the torque assembly.

In various embodiments, rotating the torque assembly relative to the hub comprises rotating the torque assembly relative to the hub such that at least one tooth of the plurality of gear teeth passes the detent mechanism.

BRIEF DESCRIPTION OF THE SEVERAL VIEWS OF THE DRAWINGS

Reference will now be made to the accompanying drawings, which are not necessarily drawn to scale, and wherein.

DETAILED DESCRIPTION

The present invention will now be described more fully hereinafter with reference to the accompanying drawings, in which some, but not all embodiments of the invention are shown. Indeed, the invention may be embodied in many different forms and should not be construed as limited to the embodiments set forth herein. Rather, these embodiments are provided so that this disclosure will satisfy applicable legal requirements. Like numbers refer to like elements throughout.

Overview

In various embodiments, a catheter guide device is provided for maintaining a catheter position while providing the ability to rotate the catheter clockwise and/or counterclockwise while in the chamber of a patient's heart or otherwise within a patient. For example, if a catheter curves after exiting the downstream end of a catheter sheath, rotating the catheter clockwise or counterclockwise relative to the sheath changes the position of the catheter within the patient. As non-limiting examples, the catheter guide device may be utilized to maintain the position of a coronary sinus catheter, lasso catheter, ultrasound catheter or ablation catheter while in the chamber of the heart. Of course, various medical uses of catheters are well-known and understood in the medical field and all should be considered within the scope and spirit of the present inventive concept.

As will be described in greater detail herein, various embodiments of the present invention may comprise a catheter guide device comprising a plurality of individual components such as a hub and/or a torque assembly comprising a gear mechanism, a locking ring, a torque device, and/or a cap. These individual components may be made of a rigid and/or resilient plastic material, although other non-limiting and exemplary materials, such as metallic and elastic materials may be utilized. Such components may be configured to be sterilized prior to use (e.g., by applying heat and/or a sterilizing chemical to the individual components). One or more components may be formed integrally relative to one another, as may be desirable, while other components may be formed separately and configured to selectively engage or interlock relative to one another so as to define the catheter guide device described herein.

In various embodiments, each of the components of the catheter guide device may be configured to be utilized only a single time prior to disposal. Such embodiments may be sterilized for a single use. Alternatively, the components of the catheter guide device may be configured to be utilized multiple times, and may be configured to be sterilized prior to each use. In other embodiments, only a portion may be disposable, while other portions may be reusable.

Catheter Control Device

Figure 1:
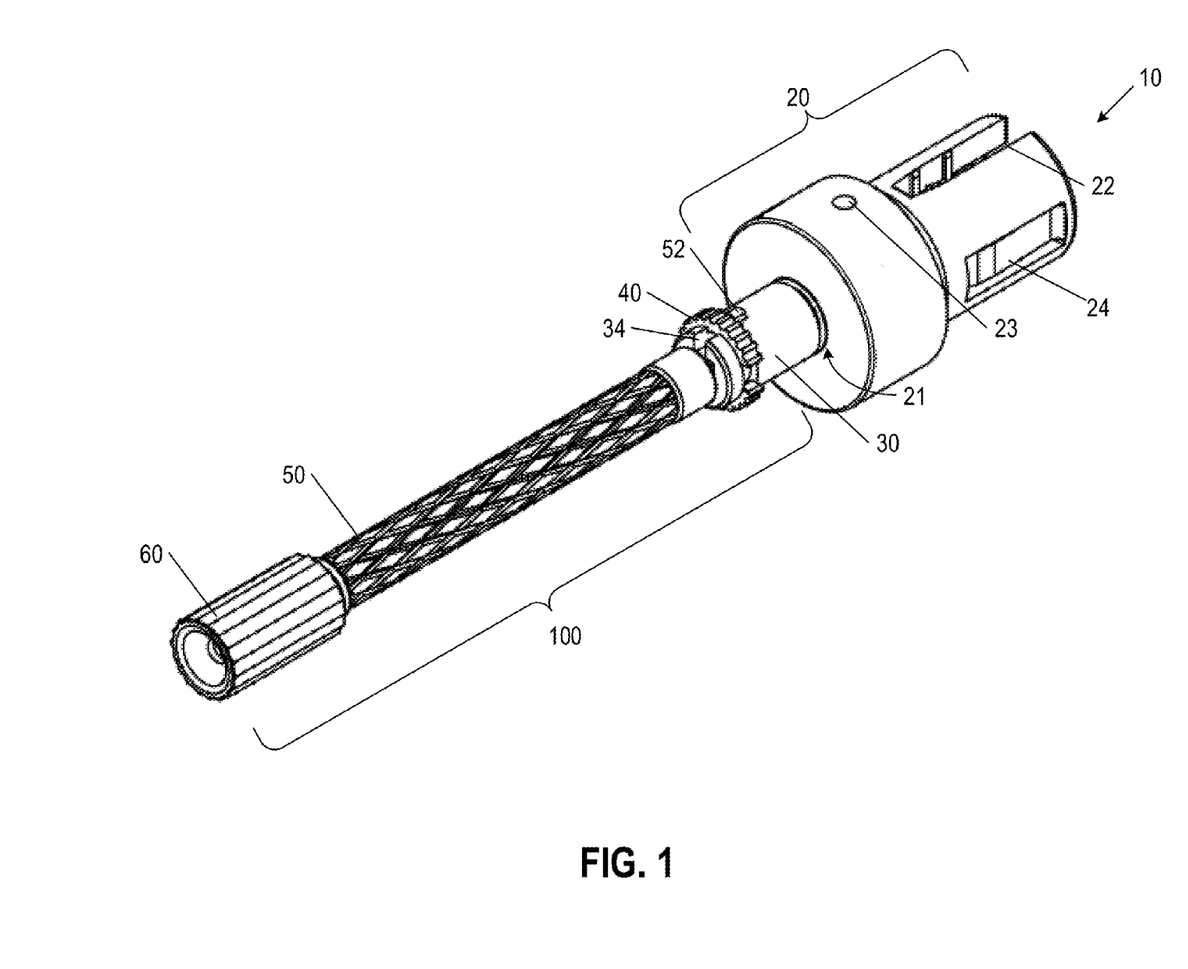
FIG. 1 shows a catheter guide device according to various embodiments.

FIG. 1 illustrates a catheter guide device 10 according to one embodiment. In the illustrated embodiment of FIG. 1, the catheter guide device 10 is configured to securely hold a catheter and catheter sheath (not shown) such that a user (e.g., a surgeon) is permitted to easily manipulate the positioning of the catheter by manipulating the positioning of various components of the catheter guide device 10. When assembled, the catheter guide device 10 may be sized such that a user can comfortably manipulate the device with one or two hands. In various embodiments, the overall length of the catheter guide device 10 may be between 100 mm and 200 mm. As a non-limiting example, the overall length of the catheter guide device 10 may be 161.5 mm, with a textured portion of a torque assembly 100 having a length of approximately 70 mm to provide a gripping surface for the user. However, various embodiments of the catheter guide device 10 may be provided in any of a variety of lengths and/or sizes without departing from the scope and spirit of the inventive concept.

Moreover, the catheter guide device 10 may be configured to securely hold catheters of various sizes, such as the non-limiting examples of 10Fr, 8Fr, 7Fr, 6Fr, and/or 5Fr. As still further non-limiting examples, the catheter guide device 10 may be configured to secure and stabilize a 10Fr (3.33 mm diameter) ultrasound catheter and/or a 7Fr/8Fr catheter in a set position while permitting the user to rotate the catheter clockwise or counterclockwise in small and/or equal increments to facilitate placement of the catheter within a patient. The catheter guide device 10 may be sized to accommodate only a single catheter size (e.g., 10Fr (3.33 mm diameter)), or it may be sized to accommodate a variety of catheter sizes, as may be desirable.

Figure 2:
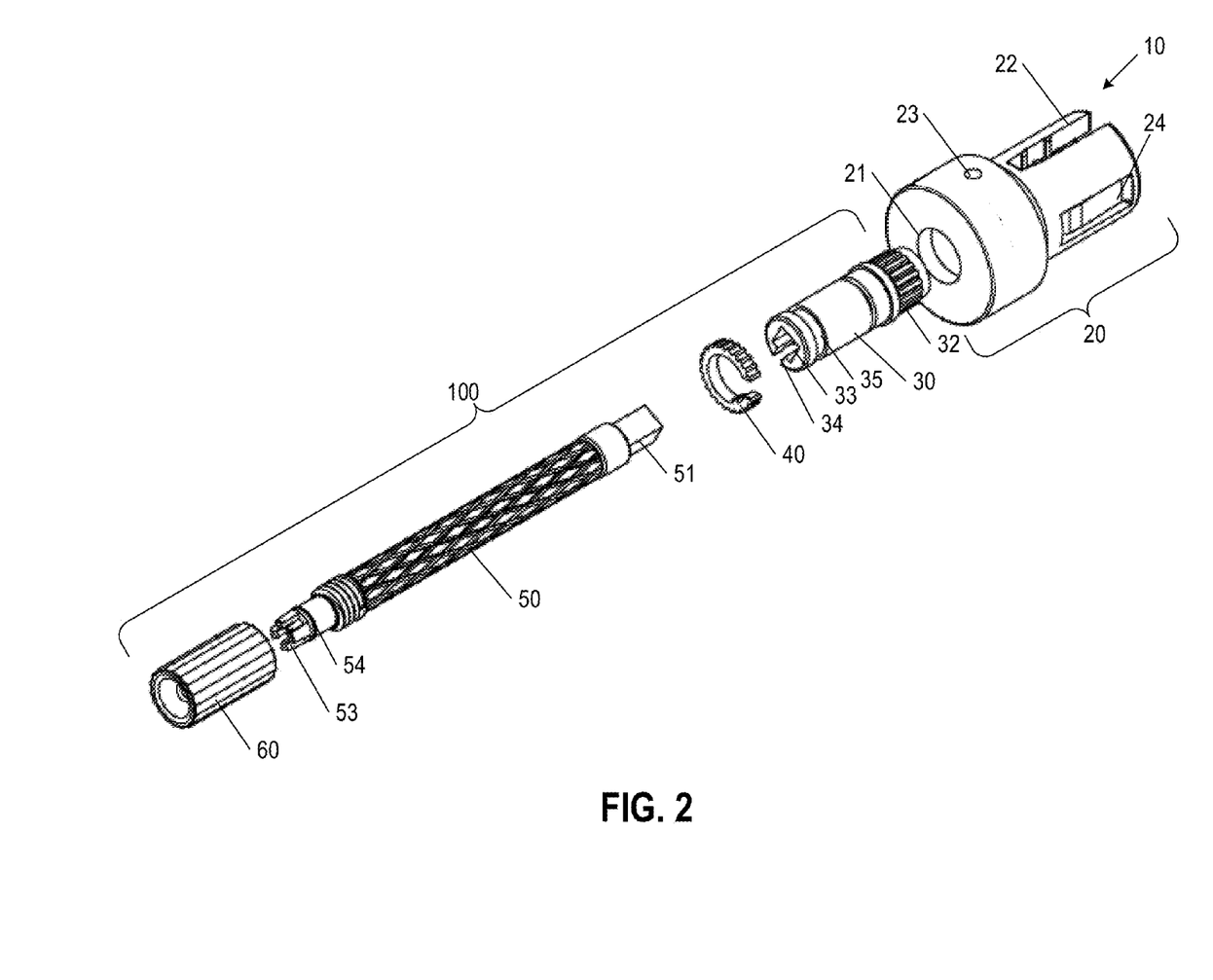
FIG. 2 shows an exploded view of the catheter guide device of FIG. 1 according to various embodiments.

Referring now to FIG. 2, which illustrates an exploded view of a catheter guide device 10 according to one embodiment, the illustrated embodiment comprises a hub 20 configured to engage a catheter sheath side port and a torque assembly 100 comprising a gear mechanism 30, a locking ring 40, a torque device 50, and an end cap 60.

In the illustrated embodiment of FIGS. 1 and 2, the hub 20 comprises a hollow cylindrical body defining an upstream end and a downstream end. As shown in FIGS. 1 and 2, the hub 20 defines an orifice 21 extending through an upstream end of the hub 20 and an open downstream end defining a hollow interior portion configured to accept a catheter sheath inserted therein. Moreover, as illustrated in FIGS. 1 and 2, the hub 20 defines a side notch 22 extending from the downstream end of the hub 20 toward the upstream end, and configured to accept a side port extending out of a side of sheath. As shown in FIGS. 1 and 2, the side notch 22 defines one or more engagement features (e.g., a ratcheting system) configured to engage the side port of the sheath and thereby impede the sheath from sliding out of the hub 20. Although not shown, in various embodiments, the side notch 22 may be angled around the perimeter of the hub 20, and/or may comprise a plurality of perpendicular segments, such that a side port must be inserted into the hub 20 so as to guide the side port through the side notch 22. Moreover, as illustrated in FIGS. 1 and 2, the hub 20 defines one or more flexible tabs 24 configured to engage (e.g., frictionally engage) a surface of a sheath to maintain the position of the sheath within the hub 20. In the illustrated embodiment, the flexible tabs 24 are configured to flex inward toward the center of the hub 20 and outward away from the center of the hub 20, and accordingly are configured to accommodate various sheath sizes and to thereby hold sheaths of a variety of sizes in place within the hub.

Thus, when rotating the hub 20, a side wall of the side notch 22 engages an exterior surface of the side port of the catheter sheath, thereby rotating and locking the catheter sheath with the hub 20. In the illustrated embodiment, the hub 20 is configured to accept and lock catheter sheaths of various sizes therein such that the catheter sheath extends away from the catheter guide device 10 in the downstream direction.

In the illustrated embodiment of FIGS. 1 and 2, the hub 20 comprises a first large diameter portion adjacent the upstream end of the hub 20 and a second small diameter portion adjacent the downstream end of the hub 20. As described in greater detail herein, the large diameter portion adjacent the upstream end of the hub 20 is configured to accept a portion of the gear mechanism 30 having a plurality of gear teeth 32 on the exterior surface thereof. The small diameter portion of the hub 20 may have a corresponding small inner diameter sized to as to permit insertion of a catheter directed toward the hemostatic valve therein.

In the illustrated embodiment of FIGS. 1 and 2, torque assembly 100 comprises a gear mechanism 30, a torque device 50, a locking ring 40 configured to secure the torque device 50 to the gear mechanism 30, and an end cap 60. The gear mechanism 30 comprises a hollow cylindrical shaft having a concentric inner lumen (e.g., an elongated central channel) having a defined diameter (e.g., configured to accept a 10Fr diameter catheter) extending along the length of the gear mechanism 30. The gear mechanism 30 further defines an upstream end and a downstream end, and comprises a plurality of gear teeth 32 on the exterior surface of the gear mechanism 30 proximate the downstream end. The gear mechanism 30 is configured to be rotatably engaged with an upstream end of the hub 20. As shown in FIGS. 1 and 2, the gear mechanism 30 may thus be positioned such that the gear mechanism extends through the orifice 21 extending through the upstream end of the hub 20 such that a portion of the gear mechanism 30 proximate the upstream end of the gear mechanism 30 protrudes through the orifice 21 of the hub 20. In the illustrated embodiment of FIGS. 1 and 2, the gear mechanism 30 cannot be detached from the hub 20 without destroying one of the hub 20 or the gear mechanism 30. However, in various embodiments, the gear mechanism 30 may be detachably secured to the hub 20. For example, in various embodiments the gear mechanism 30 is permitted to slide through the orifice 21 in the downstream direction to detach from the hub 20 when a side port is not secured in the hub 20. In such embodiments, the gear mechanism 30 may comprise one or more hub engagement ridges on an exterior surface of the gear mechanism 30 so as to prevent the gear mechanism 30 from sliding entirely through the orifice 21. As described below, the one or more hub engagement ridges may be positioned such that the plurality of gear teeth 32 are positioned within the hub 20 when the gear mechanism 30 is engaged with the hub 20.

Referring again to FIG. 1, a portion of the gear mechanism 30 proximate the downstream end of the gear mechanism 30 is positioned within an interior portion of the hub 20 such that, when assembled, the plurality of gear teeth 32 are positioned within the hub 20.

Figure 3:
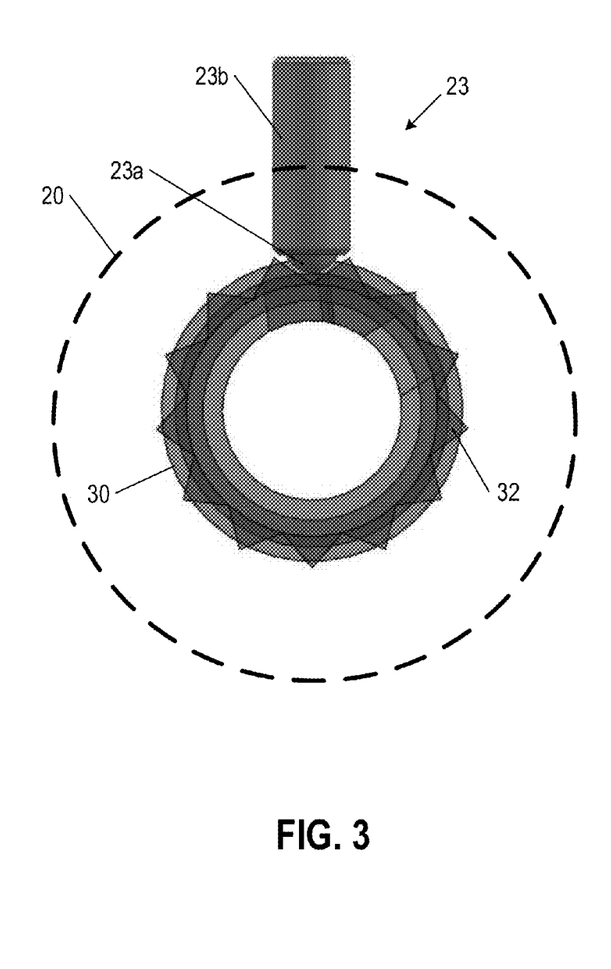
FIG. 3 illustrates the operative relationship between a detent mechanism and a plurality of gear teeth that form a portion of the catheter guide device of FIG. 1 according to various embodiments.

Referring now to FIG. 3, the interior of the hub 20 comprises a detent mechanism 23 configured to engage the plurality of gear teeth 32 and thereby provide resistance to facilitate rotation of the torque assembly 100 relative to the hub 20 in discrete intervals so as to facilitate precise placement of a downstream end of a catheter. The detent mechanism 23 thus impedes free and/or unintended rotation of the gear mechanism 30 relative to the hub 20. In various embodiments, the resistance is sufficient to prevent free and/or unintended rotation of the gear mechanism 30 relative to the hub 20 caused by, for example, fluid flows in the patient's body against the catheter, unintended jostling of the catheter guide device 10, and or the like. However, the resistance to impede rotation of the gear mechanism 30 relative to the hub 20 is sufficiently low that the user (e.g., surgeon) is permitted to rotate the gear mechanism 30 relative to the hub 20 with minimal effort.

In the illustrated embodiment, the detent mechanism 32 comprises a spring-based plunger 23a biased by the spring (not shown) in an extended position such that a distal end of the plunger 23a is positioned between two adjacent gear teeth 32 to thereby impede free rotation of the gear mechanism 30. The spring-based plunger 23a may be operable between the extended position in which a distal end of the plunger 23a is between adjacent gear teeth and a retracted position in which the distal end of the plunger 23a is positioned out of the rotational path of the gear teeth.

In various embodiments, the detent mechanism 23 additionally comprises a housing 23b for containing the spring. As illustrated, the housing 23b is an elongated hollow housing having an open end through which the distal end of the plunger 23a protrudes. In the extended position, the plunger 23a protrudes a first distance out of the housing 23b, and in the retracted position, the plunger 23a extends a second distance out of the housing 23b smaller than the first distance, such that a gear tooth is permitted to pass under the plunger 23a when in the retracted position. As the gear mechanism 30 is rotated relative to the hub 20, the distal end of the plunger 23a may be configured to engage a side surface of a gear tooth such that the plunger 23a is depressed into the retracted position as the gear tooth passes the plunger 23a. The amount of force necessary to depress the plunger 23a to the retracted position forms the resistance to impede free and/or unintended rotation of the gear mechanism 30 relative to the hub 20.

In the illustrated embodiment of FIGS. 1 and 2, the housing 23b is friction pressed into a through hole extending through a side of the hub 20. However, in various embodiments, the housing 23b is friction pressed into a blind hole formed in an interior side of the hub 20. In various embodiments, the housing 23b may be integrally formed with the hub 20 or may be secured to the hub with one or more fasteners (e.g., adhesives, rivets, ultrasonic welds, welds, spot welds, and/or the like).

However, the detent mechanism 23 may take any of a variety of forms, including a resilient and/or elastic member extending between adjacent gear teeth and configured to elastically deform as a gear tooth is rotated past the detent mechanism 23.

In various embodiments, the gear mechanism 30 may comprise a plurality of gear teeth 32 spaced at regular intervals around the outside perimeter of the gear mechanism 30. The plurality of gear teeth 32 may be spaced at regular intervals to facilitate precise movements of a downstream end of a catheter by rotating the gear mechanism 30 relative to the hub 20 such that a single gear tooth passes the detent mechanism 23. For example, if a catheter moves after placement of the catheter within the patient (e.g., after placement of an ultrasound catheter into the right atrium of a patient), rotating the torque assembly 100 relative to the hub 20 moves the downstream end of the catheter substantially clockwise or counterclockwise inside the patient. Having a small distance between adjacent gear teeth thereby translates to a small rotational (clockwise or counterclockwise) movement of the downstream end of the catheter inside the patient when rotating the torque assembly 100 relative to the hub 20 such that a single gear tooth passes the detent mechanism 23. As a non-limiting example, the gear teeth 32 may be spaced at 1mm intervals around the outside perimeter of the gear mechanism 30 to facilitate precise movement of the downstream end of the catheter inside a patient. Alternatively, in various embodiments, the gear teeth 32 may be spaced at irregular and/or alternating intervals (e.g., a 1 mm interval between a first gear tooth and an adjacent second gear tooth, and a 2 mm interval between the second gear tooth and an adjacent third gear tooth).

Referring again to FIGS. 1 and 2, in the illustrated embodiment, the gear mechanism 30 is configured to be coupled to the torque device 50 such that the torque device 50 is prevented from rotating relative to the gear mechanism 30. In the illustrated embodiment shown in FIG. 2, the torque device 50 comprises a hollow cylindrical shaft having a concentric inner lumen having a defined diameter (e.g., configured to accept a 10Fr diameter catheter) extending along the length of the torque device 50. In various embodiments, the diameter of the concentric inner lumen of the torque device 50 may correspond to the diameter of the concentric inner lumen of the gear mechanism 30 such that a catheter can pass entirely through the torque assembly 100 via the lumens extending through the torque device 50 and the gear mechanism 30. The torque device 50 may define a downstream end configured to securely engage the gear mechanism 30, and an upstream end configured to securely engage an end cap 60.

As shown in FIG. 2, the downstream end may define a non-circular protrusion 51 configured to engage non-circular bore 33 having a corresponding profile in the upstream end of the gear mechanism 30 configured to prevent relative rotation between the torque device 50 and gear mechanism 30. For example, the non-circular protrusion 51 and non-circular bore 33 may have corresponding triangular, square, pentagonal, hexagonal, elliptical, and/or other profile shapes that prevent relative rotation between the torque device 50 and gear mechanism 30.

When assembled such that the non-circular protrusion 51 of the torque device 50 is positioned within the non-circular bore 33 of the gear mechanism 30, the torque device 50 is prevented from rotating relative to the gear mechanism 30. Accordingly, by rotating the torque device 50, the gear mechanism (and the entirety of the torque assembly 100) is rotated relative to the hub 20.

Moreover, as shown in FIG. 1, the non-circular protrusion 51 may define a key member 52 extending perpendicular to the longitudinal axis of the torque device 50 and configured to engage a notch 34 on a side of the gear mechanism 30 and extending away from the upstream end of the gear mechanism 30. The key member 52 and notch 34 may be operable with a locking ring 40 to prevent the torque device 50 from disengaging the gear mechanism 30 during use of the catheter guide device 10. As shown in FIGS. 1 and 2, the locking ring 40 is configured to be positioned around the exterior diameter of the gear mechanism 30 such that the locking ring 40 is permitted to rotate relative to the gear mechanism 30, but is prevented from sliding along the length of the gear mechanism 30. For example, as shown in FIGS. 1 and 2, the locking ring 40 may be positioned within a corresponding channel extending around the exterior of the gear mechanism 30. As shown in FIGS. 1 and 2, the locking ring 40 defines an opening extending along the length of the locking ring 40 and configured to permit the key member 52 to slide through the opening of the locking ring. Thus, with the locking ring positioned such that opening is aligned with the notch 34 of the gear mechanism 30, the key member 52 may be slid through the notch 34 until the key member 52 passes the entire length of the locking ring 40. The locking ring may then be rotated such that the opening is no longer aligned with the notch 34 to prevent the torque device 50 from disengaging the gear mechanism 30. In various embodiments as shown in FIGS. 1 and 2, the locking ring 40 may have a plurality of ridges or other texture to facilitate rotation of the locking ring 40 relative to the gear mechanism 30 by a user. Likewise, the exterior surface of the torque device 50 may be textured in order to facilitate rotation of the torque assembly 100 relative to the hub 20 by the user.

Referring again to the FIGS. 1 and 2, in the illustrated embodiment, the upstream end of the torque device 50 is configured to engage an end cap 60 (e.g., by having male threads on an exterior surface of the torque device 50 proximate the upstream end of the torque device). Moreover, as shown in FIG. 2, the upstream end of the torque device 50 is split into a plurality of individual jaw members 53. Each of the jaw member 53 are resilient such that, collectively, the plurality of jaw members 53 are configured to be compressed onto the surface of a catheter sheath to firmly lock the catheter sheath into place relative to the catheter guide device 10 when the end cap 60 is engaged with the torque device 50.

In various embodiments, the end cap 60 may comprise a hollow generally cylindrical member having a tapered inner lumen having a small lumen diameter having a defined diameter (e.g., configured to accept a 10Fr diameter catheter), and a large lumen diameter proximate a downstream end of the end cap and having a diameter larger than the exterior diameter of the upstream end of the torque device 50. In the illustrated embodiment of FIGS. 1 and 2, the end cap 60 has a textured (e.g., ribbed) exterior surface in order to facilitate gripping the end cap 60. In various embodiments, a plurality of end caps 60 may be provided, each having a different small lumen diameter configured to accept catheters of various diameters. In various embodiments, each size end cap 60 may be a different color to distinguish between various end cap sizes.

In various embodiments, the small lumen diameter of the end cap 60 may correspond to the inner lumen diameter of the torque device 50 and/or the gear mechanism 30 such that a catheter may pass through the lumens defined through the entirety of the torque assembly 100. In various embodiments, the small lumen diameter of the end cap 60 may be smaller than the inner lumen diameter of the torque device 50 and/or the gear mechanism 30.

The end cap 60 may further define female threads proximate the downstream end of the end cap 60 and configured to engage corresponding male threads on an exterior surface of the torque device 50. When the end cap 60 is screwed onto the upstream end of the torque device 50, the tapered interior lumen is configured to engage the plurality of jaw members 53 and compress the jaw members, for example, onto the exterior surface of a catheter sheath. Moreover, in the illustrated embodiment of FIG. 2, the torque device 50 defines a locking ridge 54 proximate the upstream end of the torque device 50 configured to engage the end cap 60 and impede removal of the end cap 60, even when the corresponding threads of the end cap 60 and torque device 50 are disengaged. The locking ridge 54 may provide a friction connection between the end cap 60 and the torque device 50 that may be disengaged by applying a force sufficient to overcome the friction connection. Thus, a user may unscrew the end cap 60 from the torque device 50, thereby allowing the jaw members 53 to release from the exterior surface of the catheter without fully removing the end cap 60 from the torque device 50.

Method of Use

Various embodiments of the present invention are directed to methods of using a catheter guide device 10 to facilitate locking a catheter into a desired position. For example, the catheter guide device 10 may be configured for locking a coronary sinus catheter in position after insertion into the coronary sinus, locking a lasso catheter after placement into the pulmonary vein, and/or locking an ultrasound catheter at a fixed level in the right atrium, while providing the user (e.g., a surgeon) with the ability to precisely rotate the catheter clockwise and/or counter-clockwise to achieve and maintain a required catheter position in the patient. In various embodiments, the catheter guide device 10 may be engaged with an ablation catheter to provide the user with better catheter control by permitting the user to use both hands to achieve fine movements and to lock the catheter into place after the user achieves the desired catheter placement. In various embodiments, a catheter sheath may be inserted into the catheter guide device 10 such that a side port of the catheter sheath extends out of the side notch 23 of the hub such that the catheter sheath is prevented from rotating relative to the hub 20. The catheter sheath may extend away from the catheter guide device 10 in the downstream direction. The catheter may thereby be inserted into the catheter sheath through the catheter guide device 10.

Moreover, as discussed herein, the plurality of jaw members 53 located on the upstream end of the torque device 50 may be configured to frictionally engage an exterior surface of the catheter at a jaw engagement location, and thus impede movement of the catheter relative to the torque assembly 100. Once the catheter has been inserted through the catheter guide device 10 such that at least a portion of the catheter extends downstream of the catheter guide device, the end cap 60 may be tightened onto the threads of the torque device 50, causing the jaw members 53 to compress onto the catheter at the jaw engagement location.

In various embodiments, by engaging the catheter sheath at a downstream location (e.g., at the side valve) and the catheter at an upstream location (i.e., at the jaw engagement location), the catheter guide device 10 is configured to facilitate rotation and placement of the catheter inside the patient by rotating the torque assembly 100 relative to the hub 20. As discussed herein, the torque assembly 100 may be rotated in either direction relative to the hub 20 (e.g., clockwise and/or counter-clockwise). As the torque assembly 100 is rotated relative to the hub 20, the gear mechanism 30 is rotated relative to the hub 20 and the detent mechanism 23. During rotation, the detent mechanism 23 moves between the extended and retracted positions while the gears pass the plunger of the detent mechanism 23.

Once the torque assembly 100 has been rotated such that the downstream tip of the catheter sheath has reached a desired location, the detent mechanism 23 engages a plurality of gear teeth 32 by returning to the extended position between adjacent gear teeth to impede movement of the catheter away from the desired position. Thus, the detent mechanism 23 may facilitate precision placement of the catheter by impeding movement of the catheter caused by external forces.

Conclusion

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. For example, although the torque assembly 100 is described as a plurality of detachable components, various embodiments comprise a torque assembly 100 having a single component integrating the features of the torque device 50 and gear assembly 30. Although specific terms are employed herein, they are used in a generic and descriptive sense only and not for purposes of limitation.

That which is claimed:

1. A catheter guide device for facilitating precision positioning of a catheter inserted through a catheter sheath and into a patient, the catheter guide device comprising:
   a torque assembly configured to frictionally engage an exterior surface of the catheter to prevent rotation of the catheter relative to the torque assembly; and
   a hub rotatably secured to the torque assembly and configured to engage an upstream end of the catheter sheath and prevent rotation of the catheter sheath relative to the hub;
   wherein:
   the torque assembly defines a plurality of gear teeth on at least a portion of an exterior surface of the torque assembly;
   the hub comprises a detent mechanism configured to operably engage the plurality of gear teeth of the torque assembly and thereby impede free rotation of the torque assembly relative to the hub; and
   rotating the torque assembly relative to the hub rotates the catheter within the catheter sheath so as to facilitate precision positioning of the catheter.

2. The catheter guide device of claim 1, wherein the torque assembly defines a lumen extending through the length of the torque assembly and configured to accept the catheter therein.

3. The catheter guide device of claim 2, wherein the torque assembly comprises:
   a gear mechanism defining an exterior surface comprising the plurality of gear teeth; and
   a torque device detachably secured to the gear mechanism such that the torque device is prevented from rotating relative to the gear mechanism and configured to frictionally engage the exterior surface of the catheter.

4. The catheter guide device of claim 3, wherein the torque device is detachable from the gear mechanism while a catheter is positioned within the lumen extending through the torque assembly.

5. The catheter guide device of claim 4, wherein the torque assembly further comprises a locking ring rotatably secured to the gear mechanism and operable between:
   a locked position in which the torque device is prevented from detaching from the gear mechanism; and
   an unlocked position in which the torque device is permitted to detach from the gear mechanism.

6. The catheter guide device of claim 3, wherein:
   the torque assembly further comprises an end cap detachably secured to the torque device at an upstream end of the torque device; and
   the upstream end of the torque device defines a plurality of jaw members configured to be compressed onto the exterior surface of the catheter to frictionally engage the catheter when the end cap is secured onto the torque device.

7. The catheter guide device of claim 1, wherein the gear teeth are regularly spaced at 1 mm intervals on the exterior surface of the torque assembly.

8. The catheter guide device of claim 1, wherein the detent mechanism comprises a spring plunger biased to an extended position in which the spring plunger engages side surfaces of adjacent gear teeth to impede free rotation of the torque device relative to the hub; and
   wherein the spring plunger is configured to retract away from the extended position as a gear tooth passes the spring plunger.

9. The catheter guide device of claim 1, wherein the torque assembly is configured to frictionally engage an exterior surface of an ultrasound catheter inserted through the catheter sheath to facilitate positioning of the ultrasound catheter within the patient.

10. The catheter guide device of claim 1, wherein the torque assembly is configured to frictionally engage an exterior surface of an ablation catheter inserted through the catheter sheath to facilitate positioning of the ablation catheter within the patient.

11. The catheter guide device of claim 1, wherein the hub is configured to engage a side port of the catheter sheath to prevent rotation of the catheter sheath relative to the hub.

12. The catheter guide device of claim 11, wherein the hub comprises side port engagement members configured to prevent the catheter sheath from disengaging from the hub.

* * * * *